United States Patent [19]

McRae

[11] Patent Number: Plant 6,425

[45] Date of Patent: Nov. 29, 1988

[54] LILY NAMED BUFF PIXIE

[75] Inventor: Edward A. McRae, Boring, Oreg.

[73] Assignee: Melridge, Inc., Gresham, Oreg.

[21] Appl. No.: 18,918

[22] Filed: Feb. 25, 1987

[51] Int. Cl.[4] ..... A01H 5/00

[52] U.S. Cl. ..... Plt./68

[58] Field of Search ..... Plt./68

*Primary Examiner*—James R. Feyrer

*Attorney, Agent, or Firm*—Charles W. Rummler

[57] ABSTRACT

A new variety of hybrid lily plant bearing large clusters of flowers distinguished by their clear buff-orange coloration and virtual lack of spots, the flowers being of medium size, upright, and of excellent form with long persistence. The medium sized, upright flowers of this plant, with its color pattern and silhouette, make it especially suitable as a pot plant variety, completely new in the upright Asiatic divisions of lilies suited to forcing and mass commercial cultivation.

This plant is highly resistant to disease and shows high tolerance of virus; it is an excellent garden plant; and the bulbs may be precooled and forced throughout the year for pot plant production. The clone is vigorous and is a good grower and propagator.

1 Drawing Sheet

BACKGROUND OF THE NEW PLANT

This new variety of lily plant originated as seedling selected from a group of seedlings planted by me at Sandy, Oreg., and resulting from a crossing of a very short, cream colored clonal selection from the 'pastel hybrids' strain as the seed parent, with a golden orange flowered seedling from 'Connecticut Lemonglow'×'Red Carpet' (both unpatented) as the pollen parent. The object of this crossing was the production of lilies in shades of orange and gold well suited to forcing for pot plant production out-of-season, heretofore unknown in the lily breeding art.

The selected seedling of this new lily plant was asexually reproduced by me and under my direction at Sandy, Oreg., and successive generations of this variety produced by bulb scale propagation and by natural propagation from bulblets demonstrated that the novel and distinctive characteristics of the selected seedling hold true in this variety under asexual propagation from generation to generation and appear to be firmly fixed. Work with this new variety under my direction has demonstrated that it remains short and is not overly susceptible to bud abortion when forced into flower out-of-season as a pot plant, and in addition the clone possesses to a high degree the desirable characteristics of hybrid vigor, great hardiness and disease resistance, as well as all of the desired characteristics of excellence of form, color and habit.

This plant has also been found to be well suited to forcing out-of-season when the bulbs are dug at the appropriate time and properly precooled; October-dug bulbs, properly precooled and potted in January, will flower under glass in western Oregon, with no supplementary lighting and at moderate greenhouse temperatures, in an average of seventy to seventy-five days.

DESCRIPTION OF THE DRAWING

My new hybrid lily cultivar is illustrated by the accompanying full color photographic drawing, which shows a face view of a fully developed flower with the flower colors being shown as nearly true to those herein specified as is reasonably possible to obtain by conventional professional photographic procedures.

DESCRIPTION OF THE NEW PLANT

The following is a detailed description of my hybrid lily cultivar based upon observations of plants grown at Sandy, Oreg., in the middle of 1986, the nomenclature being according to The International Lily Register (The Royal Horticultural Society of London, England, 2nd Edition, 1969) and with color designations according to The R.H.S. Colour Chart published by The Royal Horticultural Society in London, England, in 1966.

THE PLANT

Origin: Seedling.

Parentage:

*Seed parent.*—A very short, cream-flowered clonal selection from the 'pastel hybrids' strain.

*Pollen parent.*—A golden orange-flowered seedling from 'Connecticut Lemonglow'×'Red Carpet' (both unpatented).

Classification:

*Botanic.*—Division I-A, upright Asiatic hybrid lily, according to The Horticultural Classification of Lilies by The Royal Horticultural Society.

*Commercial.*—Hybrid Lilium clone.

Form: Single stem, erect and stately.

Height: From about 30 to 40 cm. on stems produced by glasshouse forcing of bulbs of about 20 to 18 cm. in circumference, provided that their light levels are adequate. Low light levels may cause 'stretching'.

Growth: Vigorous and upright.

Foliage:

*Quantity.*—Abundant.

*Leaf size.*—About 9 to 12 cm. long and about 0.5 to 1 cm. wide.

*Shape of leaf.*—Lanceolate and acuminate.

*Texture.*—Leathery.

*Aspect.*—Glossy.

*Color.*—Medium green, lighter on the lower side.

The bulb:

*Size.*—Varying, ranging to about 25 cm. in circumference as commercially used.

*Color.*—White.

THE BUD

Form: Long ovoid with obtuse base and tip.

Size: About 8 to 9 cm. long and about 5 cm. in circumference just prior to opening.

Opening rate: The bud opens slowly, taking about one hour in response to morning light.

Color: Soft buff-orange with a flush of green along the midrib and at the tip prior to opening and as the tepals begin to unfurl.

Peduncle:

*Length.*—About 4 to 6 cm., in average, but may elongate if light levels are too low or if the bulbs have been improperly stored prior to forcing.

*Color.*—Medium green.

THE FLOWER

Blooming habit: Once annually, flowering profusely in midseason.

Size: The flowers average about 14 to 16 cm. in diameter.

Borne: Singly, in a compact raceme having 7 to 12 buds, from a bulb of about 12 to 16 cm. in circumference.

Shape: Cup-shaped upon first opening and becoming flattened as the tepals recurve every second day.

Tepalage: Normal, with six tepals imbricated in a slightly overlapping arrangement.

*Tepal size.*—The outer tepals average about 3 cm. wide and the inner tepals average about 3.5 cm. wide.

*Color.*—The flowers are distinguished by their clear buff-orange coloring, the base color being RHS 23B-C with a flush of deeper orange, RHS 25B, which is about 1 cm. wide and extends about 2 to 3 cm. along the midribs from the nectaries. The nectaries are soft gold, overlaid with white pubescence.

*Spotting.*—The tepals are marked with only one to three tiny, inconspicuous spots on each tepal parallel with the nectaries.

*Longevity.*—The tepals stay on the stem about three weeks.

Pedicel:

*Length.*—About 4 to 8 cm., in average.

*Form.*—Sturdy and ascending up to about 60 degrees from the horizontal.

*Color.*—Medium to dark green.

Color changes: The flower may become slightly more orange as it ages, depending upon light levels; there is usually only a slight change if the light levels are adequate for cut flower and pot plant maintenance.

Disease resistance: The flower and plant are resistant to disease, and in particularly they are resistant to Fusarium bulb rot and Botrytis blight, as observed in western Oregon.

Fragrance: None.

Lasting quality: The flowers are long lasting, both on the plant and as cut flowers.

REPRODUCTIVE ORGANS

Stamens:

*Number.*—Six, in arrangement typical of genus Lilium.

*Pollen and anthers (dehisced).*—Greyed orange, RHS 168A.

*Filaments.*—Length: About 5 cm. Color: Soft orange, RHS 25D.

Pistil:

*Number.*—One.

*Style.*—Length: About 5 cm.

*Stigma.*—Size: Small. Color: Deep plum.

Character of ovary: The ovary is typical of the genus Lilium.

THE FRUIT

Fertility: The fruit is fertile.

Shape: Ovoid.

Color at maturity: Soft brown, sometimes overlaid with soft plum.

This new variety of hybrid lily with its unique color and 'pot plant' silhouette does not closely resemble any variety in cultivation. Its habit somewhat resembles that of 'Charisma' (U.S. Plant Pat. No. 4,180) but it has a higher bud count; shorter and more abundant, lighter colored leaves and stems. It differs from 'Charisma' in its clear buff-orange color.

I claim:

1. A new and distinctive variety of Asiatic hybrid lily plant and parts thereof, substantially as herein shown and described, characterized by its virtually unspotted, clear buff-orange flowers; and by its short stemmed, longer, and abundantly leaved, upright flowering silhouette particularly suited for pot plant culture and for forcing into flower out-of-season from properly precooled bulbs.

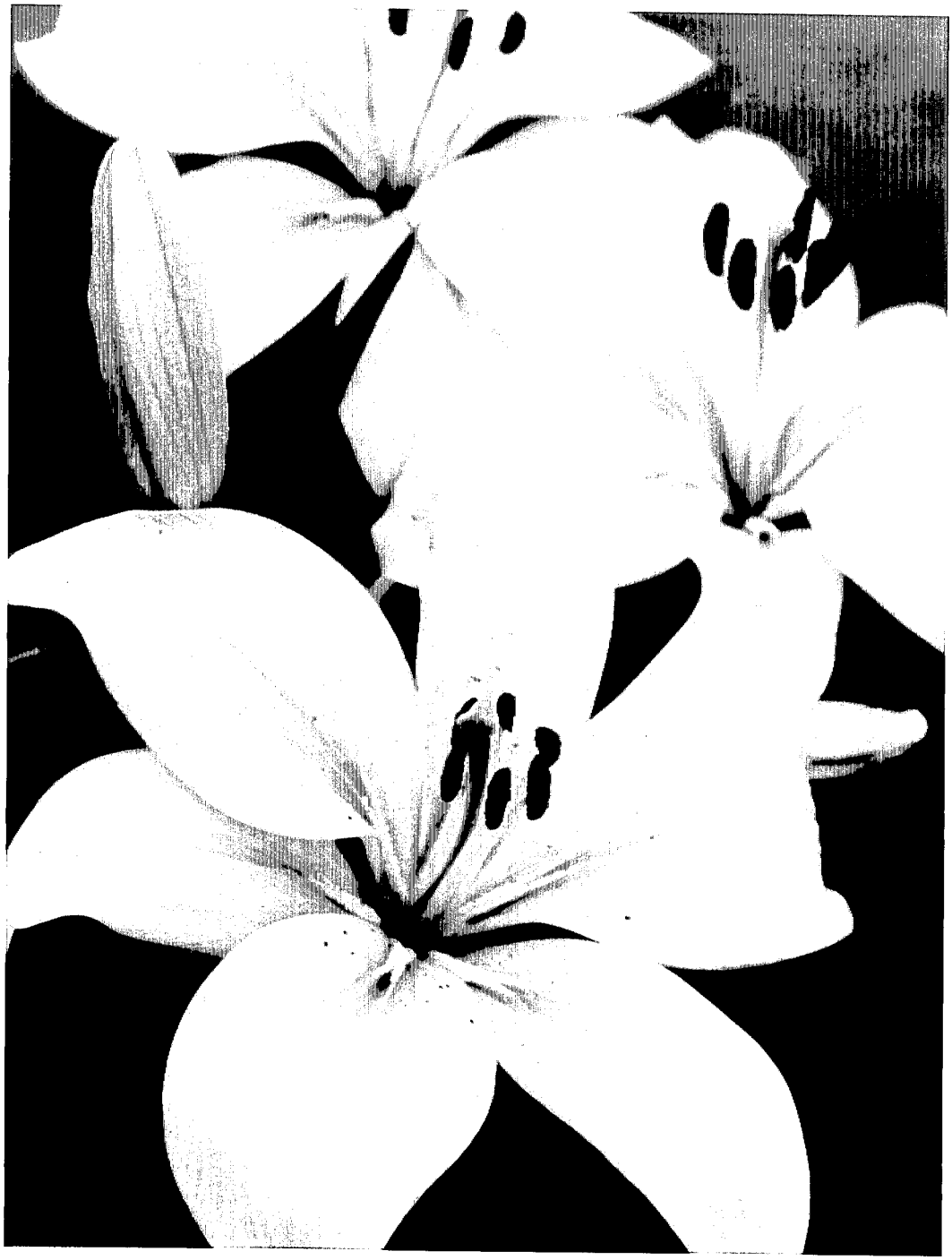

* * * * *